United States Patent
Li

(10) Patent No.: US 7,511,137 B2
(45) Date of Patent: Mar. 31, 2009

(54) STEREOISOMERS AND STEREOISOMERIC MIXTURES OF 1-(2,4-PYRIMIDINEDIAMINO)-2-CYCLOPEN-TANECARBOXAMIDE SYNTHETIC INTERMEDIATES

(75) Inventor: Hui Li, Millbrae, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 749 days.

(21) Appl. No.: 11/016,403

(22) Filed: Dec. 17, 2004

(65) Prior Publication Data

US 2005/0192301 A1     Sep. 1, 2005

Related U.S. Application Data

(60) Provisional application No. 60/572,507, filed on May 18, 2004, provisional application No. 60/531,598, filed on Dec. 19, 2003.

(51) Int. Cl.
*C07D 239/00* (2006.01)
*C07D 239/02* (2006.01)

(52) U.S. Cl. ...................................................... 544/242
(58) Field of Classification Search .................. 544/242
See application file for complete search history.

(56) References Cited

FOREIGN PATENT DOCUMENTS

| WO | WO 02/096888 | 12/2002 |
|----|--------------|---------|
| WO | WO 03/040141 | 5/2003 |
| WO | WO 03/055489 | 7/2003 |

OTHER PUBLICATIONS

Vippagunta et al., "Crystalline Solids", Adv. Drug Del. Reviews, 48 (2001) 3-26.*
PCT Search Report, Apr. 19, 2005.

* cited by examiner

*Primary Examiner*—James O. Wilson
*Assistant Examiner*—Paul V. Ward
(74) *Attorney, Agent, or Firm*—McDonnell Boehnen Hulbert & Berghoff LLP

(57) ABSTRACT

The present invention provides stereoisomers and stereoisomeric mixtures of 1-(2,4-pyrimidinediamino), 2-formamido cyclopentyl intermediates useful for the preparation of compounds having antiproliferative activity and methods to prepare the intermediates.

12 Claims, No Drawings

STEREOISOMERS AND STEREOISOMERIC MIXTURES OF 1-(2,4-PYRIMIDINEDIAMINO)-2-CYCLOPENTANECARBOXAMIDE SYNTHETIC INTERMEDIATES

1. CROSS REFERENCE TO RELATED APPLICATIONS

This application claims priority to U.S. Provisional Application 60/531,598, filed Dec. 19, 2003, entitled "Methods of Treating or Preventing Autoimmune Diseases with 2,4-Pyrimidinediamine Compounds" and U.S. Provisional Application 60/572,507, entitled "Stereoisomers and Stereoisomeric Mixtures of 1-(2,4-Pyrimidinediamino)-2-Cyclopentanecarboxamides and Uses as Anti-Proliferative Agents, filed May 18, 2004.

2. FIELD

The present invention relates to stereoisomers and stereoisomeric mixtures of 1-(2,4-pyrimidinediamino)-2-cyclopentanecarboxamide intermediates that are useful for the preparation of 1-(2,4-pyrimidinediamino)-2-cyclopentanecarboxamides that exhibit antiproliferative activity.

3. BACKGROUND

Cancer is a group of varied diseases characterized by uncontrolled growth and spread of abnormal cells. Generally, all types of cancers involve some abnormality in the control of cell growth and division. The pathways regulating cell division and/or cellular communication become altered in cancer cells such that the effects of these regulatory mechanisms in controlling and limiting cell growth fails or is bypassed. Through successive rounds of mutation and natural selection, a group of abnormal cells, generally originating from a single mutant cell, accumulates additional mutations that provide selective growth advantage over other cells, and thus evolves into a cell type that predominates in the cell mass. This process of mutation and natural selection is enhanced by genetic instability displayed by many types of cancer cells, an instability which is gained either from somatic mutations or by inheritance from the germ line. The enhanced mutability of cancerous cells increases the probability of their progression towards formation of malignant cells. As the cancer cells further evolve, some become locally invasive and then mestasize to colonize tissues other than the cancer cell's tissue of origin. This property along with the heterogeneity of the tumor cell population makes cancer a particularly difficult disease to treat and eradicate.

Traditional cancer treatments take advantage of the higher proliferative capacity of cancer cells and their increased sensitivity to DNA damage. Ionizing radiation, including γ-rays and x-rays, and cytotoxic agents, such as bleomycin, cis-platin, vinblastine, cyclophosphamide, 5'-fluorouracil, and methotrexate rely upon a generalized damage to DNA and destabilization of chromosomal structure which eventually lead to destruction of cancer cells. These treatments are particularly effective for those types of cancers that have defects in cell cycle checkpoint, which limits the ability of these cells to repair damaged DNA before undergoing cell division. The non-selective nature of these treatments, however, often results in severe and debilitating side effects. The systemic use of these drugs may result in damage to normally healthy organs and tissues, and compromise the long-term health of the patient.

Although more selective chemotherapeutic treatments have been developed based on knowledge of how cancer cells develop, for example, the anti-estrogen compound tamoxifen, the effectiveness of all chemotherapeutic treatments are subject to development of resistance to the drugs. In particular, the increased expression of cell membrane bound transporters, such as MdrI, produces a multidrug resistance phenotype characterized by increased efflux of drugs from the cell. These types of adaptation by cancer cells severely limit the effectiveness of certain classes of chemotherapeutic agents. Consequently, identification of other chemotherapeutic agents, particularly active stereoisomers and/or stereoisomeric mixtures thereof is critical for establishing therapies effective for attacking the heterogeneous nature of proliferative disease and for overcoming any resistance that may develop over the course of therapy with other compounds. Moreover, use of combinations of chemotherapeutic agents, including different stereoisomers and/or stereoisomeric mixtures of a particular chemotherapeutic agent, which may have differing properties and cellular targets, increases the effectiveness of chemotherapy and limits the generation of drug resistance.

4. SUMMARY

In one aspect, stereoisomeric mixtures of 1-(2,4-pyrimidinediamino)-2-cyclopentanecarboxamide intermediates that are useful in the preparation of antiproliferative 1-(2,4-pyrimidinediamino)-2-cyclopentanecarboxamides are described. 1-(2,4-pyrimidinediamino)-2-cyclopentanecarboxamides, such as compounds 1, 2 and 3, infra, exhibit antiproliferative activity against a variety of different cell types, including a variety of different types of tumor cells. In particular, 1-(2,4-pyrimidinediamino)-2-cyclopentanecarboxamide intermediates are provided according to structural formula (I):

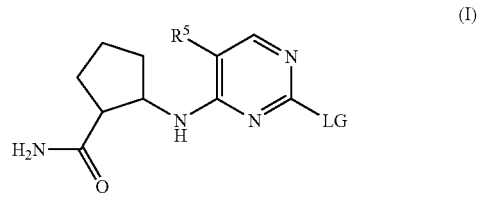

(I)

including salts, hydrates, solvates and N-oxides thereof, wherein $R^5$ is halo, fluoro, —CN, —NO$_2$, CO$_2R^a$ or —CF$_3$;

$R^a$ is selected from the group consisting of hydrogen, lower alkyl and lower cycloalkyl; and LG is a leaving group.

In another aspect, the intermediates include a compound according to structural formula (I), supra, which is enriched in one or more of the following stereoisomers according to structural formulae (II), (III) and (IV):

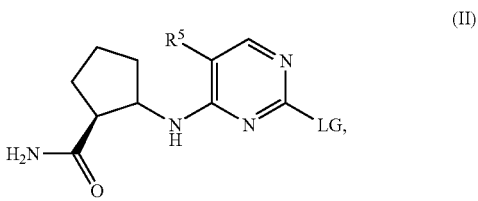

(II)

-continued

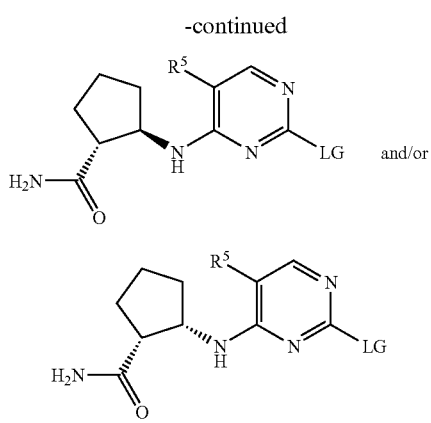

wherein R⁵ and LG are as defined for structural formula (I), supra.

In still another aspect, an intermediate according to structural formula (II) is provided:

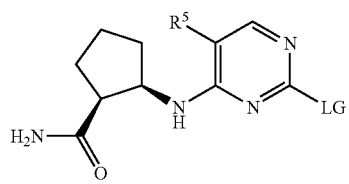

including salts, hydrates, solvates and N-oxides thereof, which is substantially free of the enantiomer and any diastereomers thereof, wherein R⁵ and LG are as defined in structural formula (I), supra.

In still another aspect, an intermediate according to structural formula (III) is provided:

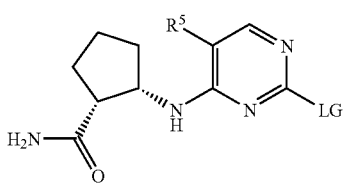

including salts, hydrates, solvates and N-oxides thereof, which is substantially free of the enantiomer and any diastereomers thereof wherein R⁵ and LG are as defined in structural formula (I), supra.

In still another aspect, an intermediate according to structural formula (IV) is provided:

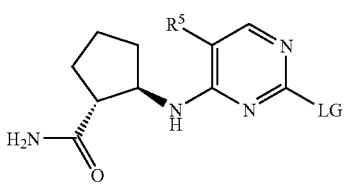

including salts, hydrates, solvates and N-oxides thereof which is substantially free of the enantiomer and any diastereomers thereof wherein R⁵ and LG are as defined for structural formula (I), supra.

In yet another aspect, formula (I) is substantially free of a compound according to structural formula (V):

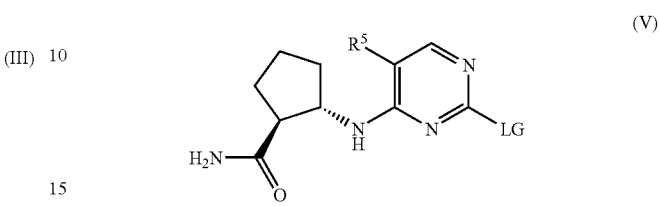

including salts, hydrates, solvates and N-oxides thereof wherein, R⁵ and LG are as defined for structural formula (I), supra.

In still another aspect, the 1-(2,4-pyrimidinediamino)-2-cyclopentanecarboxamide intermediates can be used to prepare 1-(2,4-pyrimidinediamino)-2-cyclopentanecarboxamide pharmaceutical compositions comprising one or more stereoisomers and/or stereoisomeric mixtures of an antiproliferative 1-(2,4-pyrimidinediamino)-2-cyclopentanecarboxamide and/or prodrug thereof and an appropriate carrier, excipient and/or diluent are provided. The exact nature of the carrier, excipient and/or diluent will depend upon the desired use for the pharmaceutical composition, and may range from being suitable or acceptable for veterinary uses to being suitable or acceptable for human use.

The 1-(2,4-pyrimidinediamino)-2-cyclopentanecarboxamide intermediates are useful for the preparation of some stereoisomers and/or stereoisomeric mixtures of 1-(2,4-pyrimidinediamino)-2-cyclopentanecarboxamides that are potent inhibitors of proliferation abnormal cells, such as tumor cell proliferation, in in vitro assays. Thus, active compounds prepared from intermediates of the invention are useful for inhibiting proliferation of abnormal cells, such as tumor cells. The method generally involves contacting an abnormal cell such as a tumor cell with an amount of a stereoisomer and/or stereoisomeric mixture of a 1-(2,4-pyrimidinediamino)-2-cyclopentanecarboxamide or prodrug thereof, or an acceptable salt, hydrate, solvate, N-oxide and/or pharmaceutical composition thereof, effective to inhibit its proliferation. The method may be practiced in in vitro contexts or in in vivo contexts as a therapeutic approach towards the treatment or prevention of proliferative disorders, such as tumorigenic cancers.

1-(2,4-pyrimidinediamino)-2-cyclopentanecarboxamide intermediates and methods useful for synthesizing the compounds, as will be described in more detail herein below.

5. DETAILED DESCRIPTION

5.1 Definitions

As used herein, the following terms are intended to have the following meanings:

"Alkyl" by itself or as part of another substituent refers to a saturated or unsaturated branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1

-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. "Lower alkyl" refers to alkyl groups having from 1 to 6 carbon atoms.

"Alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkyldiyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies be on the same carbon atom, the nomenclature "alkylidene" is used. A "lower alkyldiyl" is an alkyldiyl group having from 1 to 6 carbon atoms. In preferred embodiments the alkyldiyl groups are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred togas alkylenes, defined infra).

"Alkylene" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkylene is indicated in square brackets. Typical alkylene groups include, but are not limited to, methylene (methano); ethylenes such as ethano, etheno, ethyno; propylenes such as propano, prop[1]eno, propa[1,2]dieno, prop[1]yno, etc.; butylenes such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkylene group is (C1-C6) or (C1-C3) alkylene. Also preferred are straight-chain saturated alkano groups, e.g., methano, ethano, propano, butano, and the like.

"Aryl" by itself or as part of another substituent refers to a monovalent aromatic hydrocarbon group having the stated number of carbon atoms (i.e., C5-C15 means from 5 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In preferred embodiments, the aryl group is (C5-C15) aryl, with (C5-C10) being even more preferred. Particularly preferred aryls are phenyl and naphthyl.

"Arylalkyl" by itself or as part of another substituent refers to an acyclic alkyl radical in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is $(C_7-C_{30})$ arylalkyl, e.g., the alkanyl, alkenyl or alkynyl moiety of the arylalkyl group is $(C_1-C_{10})$ and the aryl moiety is $(C_6-C_{20})$, more preferably, an arylalkyl group is $(C_7-C_{20})$ arylalkyl, e.g., the alkanyl, alkenyl or alkynyl moiety of the arylalkyl group is $(C_1-C_8)$ and the aryl moiety is $(C_6-C_{12})$.

"Cycloalkyl" by itself or as part of another substituent refers to a cyclic version of an "alkyl" group. Typical cycloalkyl groups include, but are not limited to, cyclopropyl; cyclobutyls such as cyclobutanyl and cyclobutenyl; cyclopentyls such as cyclopentanyl and cycloalkenyl; cyclohexyls such as cyclohexanyl and cyclohexenyl; and the like.

"Cycloheteroalkyl" by itself or as part of another substituent refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, imidazolidine, morpholine, piperazine, piperidine, pyrazolidine, pyrrolidine, quinuclidine, and the like.

"Heteroalkyl, Heteroalkanyl, Heteroalkenyl, Heteroalkynyl" by itself or as part of another substituent refer to alkyl, alkanyl, alkenyl and alkynyl radical, respectively, in which one or more of the carbon atoms (and any associated hydrogen atoms) are each independently replaced with the same or different heteroatomic groups. Typical heteroatomic groups include, but are not limited to, —O—, —S—, —O—O—, —S—S—, —O—S—, —NR'—, =N—N=, —N=N—, —N=N—NR'—, —PH—, —P(O)$_2$—, —O—P(O)$_2$—, —S(O)—, —S(O)$_2$—, —SnH$_2$— and the like, where R' is hydrogen, alkyl, substituted alkyl, cycloalkyl, substituted cycloalkyl, aryl or substituted aryl.

"Heteroaryl" by itself or as part of another substituent, refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, benzoxazine, benzimidazole, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is from 5-20 membered heteroaryl, more preferably from 5-10 membered heteroaryl. Preferred heteroaryl groups are those derived from thiophene, pyrrole, benzothiophene, benzofuran, indole, pyridine, quinoline, imidazole, oxazole and pyrazine.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms are replaced with a halogen. Thus, the term "haloalkyl" is meant to include monohaloalkyls, dihaloalkyls, trihaloalkyls, etc. up to perhaloalkyls. For example, the expression "(C1-C2)haloalkyl" includes fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

"Hydroxyalkyl" by itself or as part of another substituent refers to an alkyl group in which one or more of the hydrogen atoms are replaced with a hydroxyl substituent. Thus, the term "hydroxyalkyl" is meant to include monohydroxyalkyls, dihydroxyalkyls, trihydroxyalkyls, etc.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, tetrahydronaphthalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, tetrahydronaphthalene, triphenylene, trinaphthalene, and the like, as well as the various hydro isomers thereof.

"Parent Heteroaromatic Ring System" refers to a parent aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Leaving group" is a group that is displaced during a reaction by a nucleophilic reagent. Suitable leaving groups include S(O)$_2$Me, —SMe or halo (e.g., F, Cl, Br, I).

"Prodrug" refers to a derivative of an active 1-(2,4-pyrimidinediamino)-2-cyclopentanecarboxamide (drug) that may require a transformation under the conditions of use, such as within the body, to release the active drug. Prodrugs are frequently, but not necessarily, pharmacologically inactive until converted into the active drug. Prodrugs are typically obtained by masking a functional group in the 1-(2,4-pyrimidinediamino)-2-cyclopentanecarboxamides believed to be in part required for activity with a progroup (defined below) to form a promoiety which undergoes a transformation, such as cleavage, under the specified conditions of use to release the functional group, and hence the active drug. The cleavage of the promoiety may proceed spontaneously, such as by way of a hydrolysis reaction, or it may be catalyzed or induced by another agent, such as by an enzyme, by light, by acid or base, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

A wide variety of progroups, as well as the resultant promoieties, suitable for masking functional groups in the 1-(2,4-pyrimidinediamino)-2-cyclopentanecarboxamide active compounds to yield prodrugs are well-known in the art. For example, a hydroxyl functional group may be masked as a sulfonate, ester or carbonate promoiety, which may be hydrolyzed in vivo to provide the hydroxyl group. An amino functional group may be masked as an amide, carbamate, imine, urea, phosphenyl, phosphoryl or sulfenyl promoiety, which may be hydrolyzed in vivo to provide the amino group. A carboxyl group may be masked as an ester (including silyl esters and thioesters), amide or hydrazide promoiety, which may be hydrolyzed in vivo to provide the carboxyl group. Other specific examples of suitable progroups and their respective promoieties will be apparent to those of skill in the art.

"Progroup" refers to a type of protecting group that, when used to mask a functional group within an active 1-(2,4-pyrimidinediamino)-2-cyclopentane carboxamide to form a promoiety, converts the intermediate into a prodrug. Progroups are typically attached to the functional group of the intermediate via bonds that are cleavable under specified conditions of use. Thus, a progroup is that portion of a promoiety that cleaves to release the functional group under the specified conditions of use. As a specific example, an amide promoiety of the formula —NH—C(O)CH$_3$ comprises the progroup —C(O)CH$_3$.

"Proliferative disorder" refers to a disease or disorder characterized by aberrant cell proliferation, for example, where cells divide more than their counterpart normal cells. The aberrant proliferation may be caused by any mechanism of action or combination of mechanisms of action. For example, the cell cycle of one or more cells may be affected such that cell(s) divide more frequently than their counterpart normal cells, or alternatively, one or more cells may bypass inhibitory signals, which would normally limit their number of divisions. Proliferative diseases include, but are not limited to, slow or fast growing tumors and cancers.

"Antiproliferative compound" refers to a compound that inhibits the proliferation of a cell as compared to an untreated control cell of a similar type. The inhibition can be brought about by any mechanism or combination of mechanisms, and may operate to inhibit proliferation cytostatically or cytotoxically. As a specific example, inhibition as used herein includes, but is not limited to, arrest of cell division, a reduction in the rate of cell division, proliferation and/or growth and/or induction of cell death.

"Pharmaceutically effective amount" or "therapeutically effective amount" refers to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or to decrease the growth rate of the tumor.

5.2 Antiproliferative Stereoisomers and Stereoisomeric Mixtures of 1-(2,4-Pyrimidinediamino)-2-Cyclopentane Carboxamides The racemic mixture of the cis isomers comprised of cis (1S, 2R) (1) and cis (1S, 2R) (2), infra, have been shown to be active against a variety of tumor cell lines in conventional antiproliferative assays as disclosed in Argade et al., entitled "2,4 Pyrimidinediamine Compounds and Uses as Anti-Proliferative Agents," U.S. Provisional Application Ser. No. 60/572,534, filed May 18, 2004. It has been discovered (see Example 6) that the trans (1R, 2R ) (3) and the individual stereoisomers (i.e., cis (1S, 2R) (1) and cis (1S, 2R) (2)) of the cis racemic mixture are active against a variety of tumor cell lines in conventional antiproliferative assays while the trans (1S, 2S) (4) is inactive in the same antiproliferation assays. Accordingly, stereoisomers of related 1-(2,4-pyrimidinediamino)-2-cyclopentanecarboxamides are expected to have analogous activity in antiproliferative assays.

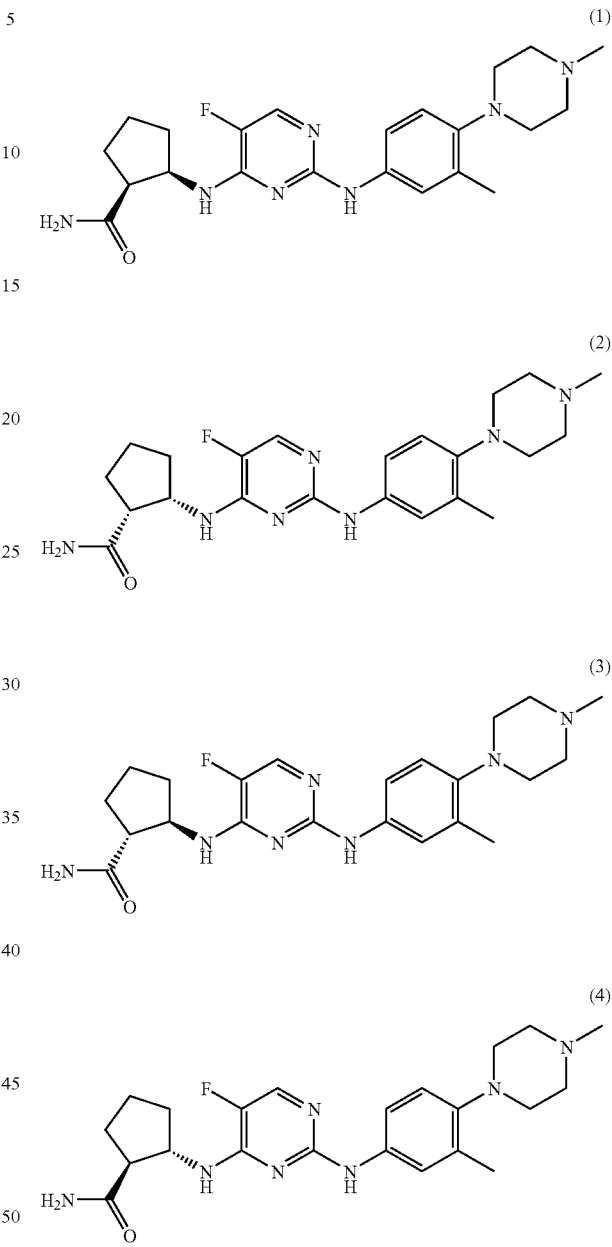

Accordingly, intermediates useful to prepare stereoisomers of 1-(2,4-pyrimidinediamino)-2-cyclopentanecarboxamides and mixtures enriched in the antiproliferative stereoisomers of 1-(2,4-pyrimidinediamino)-2-cyclopentanecarboxamide are provided herein.

Accordingly, those of skill in the art will appreciate that intermediates useful for the preparation of antiproliferative stereoisomers of 1-(2,4-pyrimidinediamino)-2-cyclopentanecarboxamides (i.e., cis (1R, 2S), cis (1S, 2R) and trans (1R, 2R)) are strongly preferred over the inactive stereoisomer intermediates (i.e., trans (1S, 2S)) both as isolated stereoisomers and as components of stereoisomeric mixtures.

Intermediates include 1-(2,4-pyrimidinediamino)-2-cyclopentanecarboxamides according to structural formula (I):

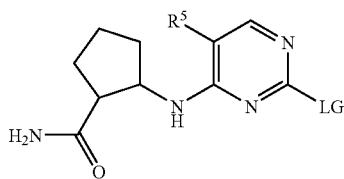

(I)

including salts, hydrates, solvates and N-oxides thereof, wherein:

$R^5$ is halo, fluoro, —CN, —NO$_2$, CO$_2$R$^a$ or —CF$_3$;

$R^a$ is selected from the group consisting of hydrogen, lower alkyl and lower cycloalkyl; and LG is a leaving group.

In some embodiments, the compound of structural formula (I) is not a racemic mixture of the cis isomers (II) and (III).

In another aspect, the intermediate includes compounds according to structural formula (I) as defined, supra, which is enriched in one or more of the following stereoisomers according to structural formula (II), (III) and (IV):

(II)

(IV) and/or (III)

wherein $R^5$ and LG are as defined for structural formula (I), supra. In some embodiments, the intermediate of structural formula (I) is enriched in the stereoisomer according to structural formula (II). In some other embodiments, the intermediate of structural formula (I) is enriched in the stereoisomer according to structural formula (III). In yet other embodiments, the intermediate of structural formula (I) is enriched in the stereoisomer according to structural formula (IV).

Below, 1-(2,4-pyrimidinediamino), 2-formamido cyclopentyl intermediates substantially free of other stereoisomers are described. One stereoisomer intermediate is a compound according to structural formula (II):

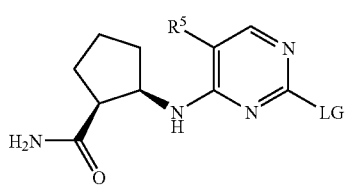

(II)

including salts, hydrates, solvates and N-oxides thereof which is substantially free of the enantiomer and any diastereomers thereof, wherein $R^5$ and LG are as defined for structural formula (I), supra.

Another stereoisomer intermediate is a compound according to structural formula (III):

(III)

including salts, hydrates, solvates and N-oxides thereof which is substantially free of the enantiomer and any diastereomers thereof wherein $R^5$ and LG are as defined for structural formula (I), supra.

Still another intermediate stereoisomer is a compound according to structural formula (IV):

(IV)

including salts, hydrates, solvates and N-oxides thereof which is substantially free of the enantiomer and any diastereomers thereof wherein $R^5$ and LG are as defined for structural formula (I), supra.

Still yet, another intermediate stereoisomer is a compound according to structural formula (V):

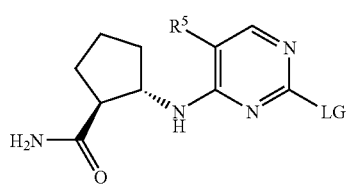

including salts, hydrates, solvates and N-oxides thereof wherein, $R^5$ and LG are as defined for structural formula (I), supra.

In one aspect, formula (I) is substantially free of a compound according to structural formula (V) including salts, hydrates, solvates and N-oxides thereof wherein, $R^5$ and LG are as defined for structural formula (I), supra.

In one embodiment of the antiproliferative compounds according to structural formulae (I), (II), (III), (IV) and (V), supra, $R^5$ is fluoro.

Those of skill in the art will appreciate that many of the intermediates described herein, as well as the various species specifically described and/or illustrated herein, may exhibit the phenomena of tautomerism and conformational isomerism. For example, the intermediates may exist in several tautomeric forms, including the enol form, the keto form and mixtures thereof. As the various compound names, formulae and compound drawings within the specification and claims can represent only one of the possible tautomeric or conformational forms, it should be understood that the invention encompasses any tautomers or conformational isomers, of the compounds having one or more of the utilities described herein, as well as mixtures of these various different isomeric forms.

Depending upon the nature of the various substituents, the 1-(2,4-pyrimidinediamino)-2-cyclopentanecarboxamide intermediates may be in the form of salts. Such salts may be derived from acids or bases, as is well-known in the art.

In some embodiments, the salt is a pharmaceutically acceptable salt. Generally, pharmaceutically acceptable salts are those salts that retain substantially one or more of the desired pharmacological activities of the parent compound and which are suitable for administration to humans. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydriodic, etc.), sulfuric acid, nitric acid, phosphoric acid, and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion or an aluminum ion) or coordinates with an organic base (e.g., ethanolamine, diethanolamine, triethanolamine, N-methylglucamine, morpholine, piperidine, dimethylamine, diethylamine, etc.).

The 1-(2,4-pyrimidinediamino)-2-cyclopentanecarboxamide intermediates, as well as the salts thereof, may also be in the form of hydrates, solvates and N-oxides, as are well-known in the art.

Stereoisomeric purity of intermediates and prodrugs described herein may be established by conventional analytical methods well known to those of skill in the art. For example, use of chiral NMR shift reagents, gas chromatographic analysis using chiral columns, high pressure liquid chromatographic analysis using chiral columns, formation of diastereomeric derivatives through reaction with chiral reagents and conventional analysis may be used to establish the stereochemical purity of a specific stereoisomer. Alternatively, synthesis using starting materials of known stereochemical enrichment may be used to establish the stereochemical purity of the compounds described herein. Other analytical methods for demonstrating stereochemical homogeneity are well within the ambit of the skilled artisan.

"Substantially free" as used herein means a compound or stereoisomeric mixture which has less than about 10% of the undesired impurities (i.e., other diastereomers or enantiomers) as established by conventional analytical methods routinely used by those of skill in the art. In some embodiments, the amount of undesired stereoisomer(s) may be less than 10%, for example, less than 9%, 8%, 7%, 6%, 5%, 4%, 3%, 2%, 1% or even less than 1%.

"Enriched in one or more of the following stereoisomers" as used herein means that at least one of the described stereoisomers is present in excess over any other stereoisomer.

Because of their activity in conventional cell proliferation assays, preferred stereoisomeric compounds formed from intermediates of structural formula (I), either alone or as part of a mixture of stereoisomers, include compounds of structural formulae (II), (III) and (IV) which are of the cis (1S, 2R), cis (1R, 2S) and the trans (1R, 2R) configuration, respectively. Stereoisomeric compounds formed from an intermediate corresponding to structural formula (V), which has the trans (1S, 2S) configuration are not preferred, either alone or as part of a mixture of stereoisomers, because of inactivity in conventional cell proliferation assays.

5.3 Methods of Synthesis

The 1-(2,4-pyrimidinediamino)-2-cyclopentane carboxamide intermediates may be synthesized via a variety of different synthetic routes using commercially available starting materials and/or starting materials prepared by conventional synthetic methods.

A variety of exemplary synthetic routes that can be used to synthesize the 1-(2,4-pyrimidinediamino)-2-cyclopentanecarboxamide intermediates and active 1-(2,4-pyrimidinediamino)-2-cyclopentanecarboxamide compounds possessing antiproliferative activity are described in Schemes (I)-(III), below. In Schemes (I)-(III), like-numbered compounds have similar structures.

In one exemplary embodiment, the intermediates can be synthesized from substituted or unsubstituted uracils or thiouracils as illustrated in Scheme (I), below:

Scheme (I)

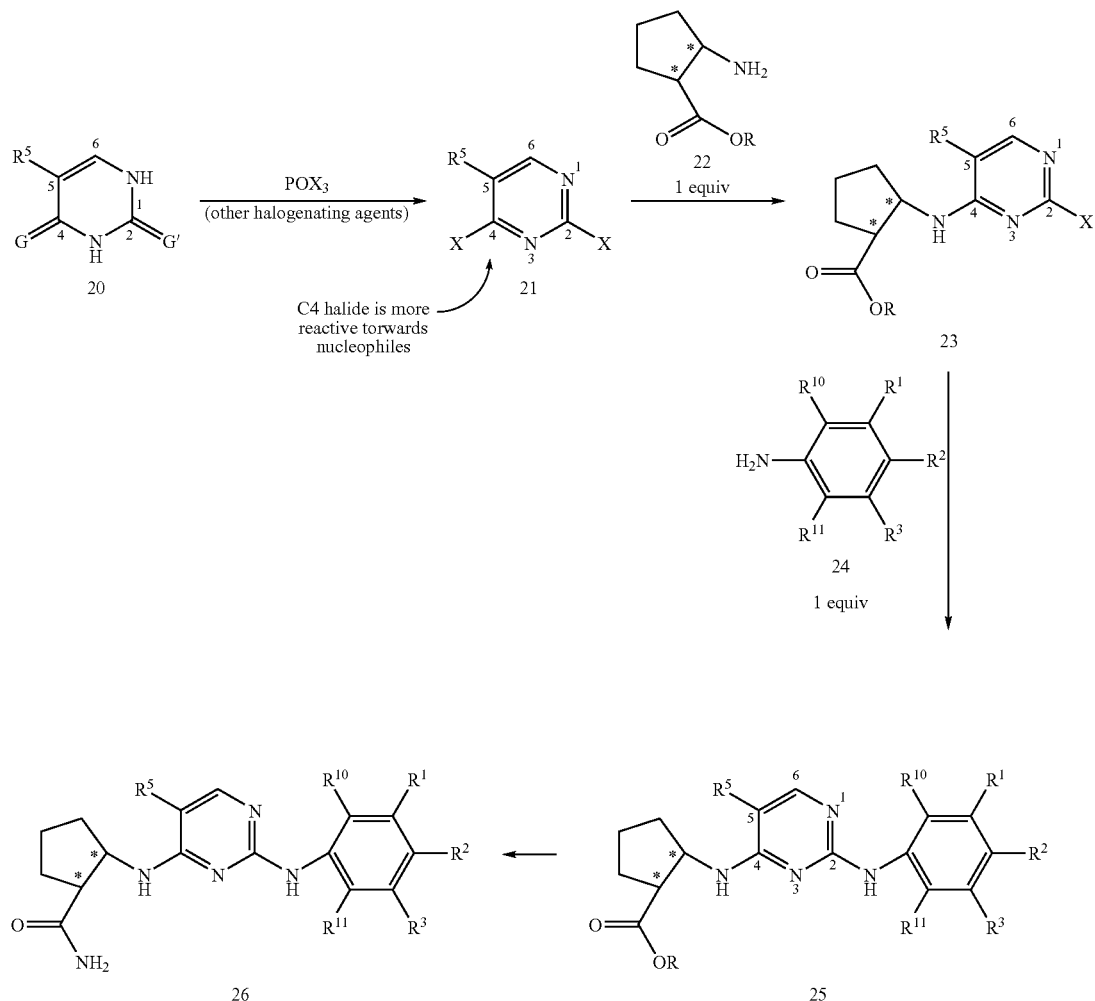

In Scheme (I), $R^5$ is as previously defined for structural formula (I), supra, X is a halogen (e.g., F, Cl, Br or I), R is H or alkyl, G and G' are each, independently of one another, selected from the group consisting of O and S, $R^1$, $R^2$, $R^3$, $R^{10}$ and $R^{11}$ are each independently selected from the group consisting of hydrogen, —OH, —SH, —CN, —NO$_2$, —N$_3$, halo, fluoro, chloro, bromo, iodo, lower alkyl, substituted lower alkyl, lower heteroalkyl, substituted lower heteroalkyl, cycloalkyl, substituted cycloalkyl, cycloheteroalkyl, substituted cycloheteroalkyl, lower haloalkyl, monohalomethyl, dihalomethyl, trihalomethyl, trifluoromethyl, lower alkylthio, substituted lower alkylthio, lower alkoxy, substituted lower alkoxy, methoxy, substituted methoxy, lower heteroalkoxy, substituted lower heteroalkoxy, cycloalkoxy, substituted cycloalkoxy, cycloheteroalkoxy, substituted cycloheteroalkoxy, lower haloalkoxy, monohalomethoxy, dihalomethoxy, trihalomethoxy, trifluoromethoxy, amino, lower di- or monoalkylamino, substituted lower di- or monoalkylamino, aryl, substituted aryl, aryloxy, substituted aryloxy, phenoxy, substituted phenoxy, arylalkyl, substituted arylalkyl, arylalkyloxy, substituted arylalkyloxy, benzyl, benzyloxy, heteroaryl, substituted heteroaryl, heteroaryloxy, substituted heteroaryloxy, heteroarylalkyl, substituted heteroarylalkyl, heteroarylalkyloxy, substituted heteroarylalkyloxy, carboxyl, lower alkoxycarbonyl, substituted lower alkoxycarbonyl, aryloxycarbonyl, substituted aryloxycarbonyl, arylalkyloxycarbonyl, substituted arylalkyloxycarbonyl, carbamate, substituted carbamate, carbamoyl, substituted carbamoyl, sulfamoyl and substituted sulfamoyl.

In particular embodiments, each $R^1$ is independently selected from the group consisting of hydrogen, lower alkyl, —(CH$_2$)$_n$—OH, —OR$^a$, —O(CH$_2$)$_n$—R$^a$, —O(CH$_2$)$_n$—R$^b$, —C(O)OR$^a$, halo, —CF$_3$ and —OCF$_3$;

each $R^2$ is independently selected from the group consisting of hydrogen, lower alkyl, —OR$^a$, —O(CH$_2$)$_n$—R$^a$, —O(CH$_2$)$_n$—R$^b$, —NHC(O)R$^a$, halo, —CF$_3$, —OCF$_3$,

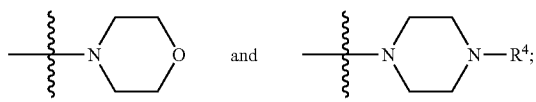

each R³ is independently selected from the group consisting of hydrogen, lower alkyl, —(CH₂)ₙ—OH, —ORᵃ, —O(CH₂)ₙ—Rᵃ, —O(CH₂)ₙ—Rᵇ, halo, —CF₃, —OCF₃,

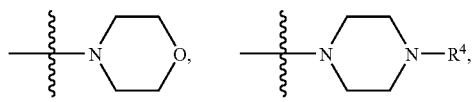

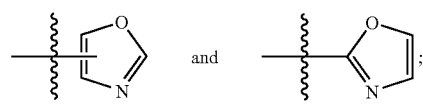

each R⁴ is independently selected from the group consisting of lower alkyl, arylalkyl, —ORᵃ, —NRᶜRᶜ, —C(O)Rᵃ, —C(O)ORᵃ and —C(O)NRᶜRᶜ;

each n is independently an integer from 1 to 3;

each Rᵃ is independently selected from the group consisting of hydrogen, lower alkyl and lower cycloalkyl;

each Rᵇ is independently selected from the group consisting of —ORᵃ, —CF₃, —OCF₃, —NRᶜRᶜ, —C(O)Rᵃ, —C(O)ORᵃ, —C(O)NRᶜRᶜ and —C(O)NRᵃRᵈ;

each Rᶜ is independently selected from the group consisting of hydrogen and lower alkyl, or, alternatively, two Rᶜ substituents may be taken together with the nitrogen atom to which they are bonded to form a 5-7 membered saturated ring which optionally includes 1-2 additional heteroatomic groups selected from O, NRᵃ, NRᵃ—C(O)Rᵃ, NRᵃ—C(O)ORᵃ and NRᵃ—C(O)NRᵃ; and each Rᵈ is independently lower mono-hydroxyalkyl or lower di-hydroxyalkyl.

It should be noted that virtually any nucleophilic containing moiety can serve as an agent to displace the leaving group, LG. For example, the nucleophile can be an amine that is part of an aryl group, a heteroaryl group, etc. For exemplary purposes only, Schemes I and III show substituted anilines. This is not meant to be limiting but serves to demonstrate that aniline compounds serve as moieties suitable for the preparation of 1-(2,4-pyrimidinediamino)-2-cyclopentanecarboxamides. Compounds that can be prepared by the methods outlined in the present application include those disclosed in WO 03/063794, WO2004/014382 and PCT/US2004/24716, the contents of which are incorporated herein by reference.

It should be noted that the "*" in amine 22 indicates that the stereocenter is not specified. Accordingly, those of skill in the art will appreciate that Schemes (I), supra, and Schemes (II) and (III), infra, may be used to prepare diastereomeric mixtures and racemic mixtures of final product 26 as well as stereoisomers of 26 substantially free of the antipode or other diastereomers.

Referring to Scheme (I), uracil or thiouracil 20 is dihalogenated at the 2- and 4-positions using the standard halogenating agent POX₃ (or other standard halogenating agents) under standard conditions to yield 2,4-bis-halo pyrimidine 21. The halide at the C4 position is more reactive towards nucleophiles than the halide at the C2 position in pyrimidine 21. This differential reactivity can be exploited to synthesize 1-(2,4-pyrimidinediamino)-2-cyclopentanecarboxamides by first reacting 2,4-bis-halopyrimidine 21 with one equivalent of aminocyclopentane 22, yielding 23, followed by reaction with aniline 24 to yield compound 25. Compound 25 may be converted to formamide 26 by use of conventional chemistry known to those of skill in the art. Those of skill in the art will appreciate that the stereoisomeric configuration and optical purity of the starting aminocyclopentane 22 will, in most circumstances, determine the stereoisomeric configuration and optical purity of the final product, 1-(2,4-pyrimidinediamino)-2-cyclopentylcarboxamide 26.

In most situations, the C4 halide is more reactive towards nucleophiles, as illustrated in the Scheme. However, as will be recognized by skilled artisans, the identity of the R⁵ substituent may alter this reactivity. For example, when R⁵ is trifluoromethyl, a 50:50 mixture of 4N-substituted-4-pyrimidineamine 23 and the corresponding 2N-substituted-2-pyrimidineamine is obtained. Regardless of the identity of the R⁵ substituent, the regioselectivity of the reaction can be controlled by adjusting the solvent and other synthetic conditions (such as temperature), as is well-known in the art.

The reactions depicted in Scheme (I) may proceed more quickly when the reaction mixtures are heated via microwave. When heating in this fashion, the following conditions may be used: heat to 175° C. in ethanol for 5-20 min. in a Smith Reactor (Personal Chemistry) in a sealed tube (at 20 bar pressure).

The uracil or thiouracil 20 starting materials may be purchased from commercial sources or prepared using standard techniques of organic chemistry. Commercially available uracils and thiouracils that can be used as starting materials in Scheme (I) include, by way of example and not limitation, uracil (Aldrich #13,078-8; CAS Registry 66-22-8); 2-thiouracil (Aldrich #11,558-4; CAS Registry 141-90-2); 2,4-dithiouracil (Aldrich #15,846-1; CAS Registry 2001-93-6); 5-bromouracil (Aldrich #85,247-3; CAS Registry 51-20-7; 5-fluorouracil (Aldrich #85,847-1; CAS Registry 51-21-8); 5-iodouracil (Aldrich #85,785-8; CAS Registry 696-07-1); 5-nitrouracil (Aldrich #85,276-7; CAS Registry 611-08-5); 5-(trifluoromethyl)-uracil (Aldrich #22,327-1; CAS Registry 54-20-6). Additional 5-substituted uracils and/or thiouracils are available from General Intermediates of Canada, Inc., Edmonton, Calif. (www.generalintermediates.com) and/or Interchim, Cedex, France (www.interchim.com), or may be prepared using standard techniques. Myriad textbook references teaching suitable synthetic methods are provided infra.

Anilines 24 may be purchased from commercial sources or, alternatively, may be synthesized utilizing standard techniques. For example, suitable anilines may be synthesized from nitro precursors using standard chemistry. Specific exemplary reactions are provided in the Examples section. See also Vogel, 1989, *Practical Organic Chemistry*, Addison Wesley Longman, Ltd. and John Wiley & Sons, Inc.

Aminocyclopentanes 22 are readily available as a mixture of diastereomers, a mixture of racemates or enantiomerically enriched see, e.g., Amarego et al., *J. Chem. Soc. C* 1970, 1597-1600; Yamazaki et al., *J. Org. Chem.* 1991, 54, 6644-6655; Szakonyi et al., *Tetrahedron: Asymmetry* 1998, 9, 993-999; Kanerva et al., *Tetrahedron: Asymmnetry* 1996, 7, 1705-1716; Csosmos et al., *Tetrahedron: Asymmetry* 1996, 7, 1789-1796; Enders et al., *Liebigs Ann./Recueil* 1997, 699-706; O'Brien et al., *Synlett* 2000, 1336-1338; Konusu et al., *Chem.*

Pharm. Bull. 1993, 41, 1012-1018; Szakonyi et al., *Tetrahedron: Asymmetry* 2000, 11, 4571-4579; Davies et al., *Synlett* 1993, 461-462; Price, *Synlett* 1999, 1919-1920; Aggarwal et al., *Org. Biomol. Chem.* 2003, 1, 684-691; Perlmutter et al., *Eur. J. Org. Chem.* 2000, 756-760; and Chippindale et al., *Tetrahedron* 2003, 59, 3253-3265. The enantiomerically enriched antipodes of aminocyclopentanes 22 may be prepared via resolution techniques, use of chiral auxiliaries, enzymatic resolution and asymmetric synthesis as taught in the references, supra. Accordingly, it well with the ambit of those of ordinary skill in the art to make any of the possible stereoisomers or stereoisomeric mixtures of the 1-(2,4-pyrimidinediamino), 2-formamido cyclopentyl compound 26 in view of the availability of the stereoisomers of amine 22 (see, e.g., Examples 1-5).

Skilled artisans will recognize that in some instances, anilines 24 may include functional groups that require protection during synthesis. The exact identity of any protecting group(s) used will depend upon the identity of the functional group being protected, and will be apparent to these of skill in the art. Guidance for selecting appropriate protecting groups, as well as synthetic strategies for their attachment and removal, may be found, for example, in Greene & Wuts, *Protective Groups in Organic Synthesis*, 3d Edition, John Wiley & Sons, Inc., New York (1999) and the references cited therein (hereinafter "Greene & Wuts").

In another exemplary embodiment, 1-(2,4-pyrimidinediamino)-2-cyclopentanecarboxamide intermediates may be synthesized from substituted or unsubstituted 2-amino-4-pyrimidinols as illustrated in Scheme (II), below:

In Scheme (II), R, $R^1$, $R^2$, $R^3$, $R^5$, $R^{10}$ and $R^{11}$ are as previously defined in Scheme (I) and Z is a leaving group. Suitable leaving groups Z include, but are not limited to, halogens, methanesulfonyloxy (mesyloxy; "OMs"), trifluoromethanesulfonyloxy ("OTf") and p-toluenesulfonyloxy (tosyloxy; "OTs"), benzene sulfonyloxy ("besylate") and metanitro benzene sulfonyloxy ("nosylate"). Other suitable leaving groups will be apparent to those of skill in the art.

Referring to Scheme (II), 2-amino-4-pyrimidinol 27 is reacted with aryl halide 28 to yield N2-substituted-4-pyrimidinol 29, which is then halogenated as previously described to yield N2-substituted-4-halo-2-pyrimidineamine 30. Reaction with amine 22 affords compound 25, which may be converted to desired 1-(2,4-pyrimidinediamino)-2-cyclopentanecarboxamides 26 by conventional methods.

Suitable commercially-available 2-amino-4-pyrimidinols 27 that can be used as starting materials in Scheme (III) are available from General Intermediates of Canada, Inc., Edmonton, Calif. (www.generalintermediates.com) and/or Interchim, Cedex, France (www.interchim.com), or may be prepared using standard techniques. Myriad textbook references teaching suitable synthetic methods are provided infra.

In yet another exemplary embodiment, 1-(2,4-pyrimidinediamino)-2-cyclopentanecarboxamides can be prepared from substituted or unsubstituted uridines as illustrated in Scheme (III) below:

Scheme (II)

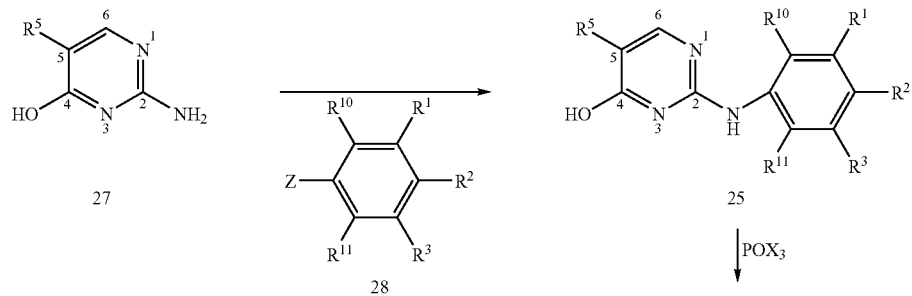

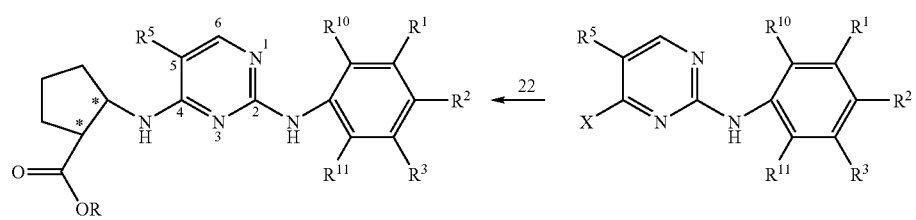

Scheme (III)

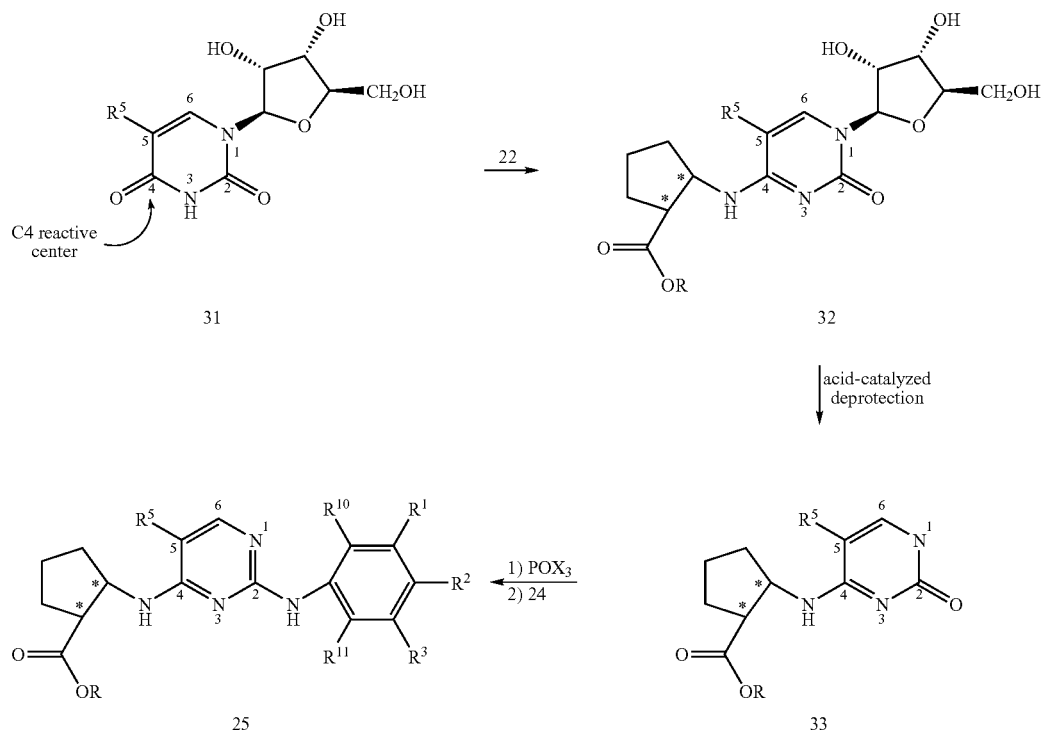

In Scheme (III), R, $R^1$, $R^2$, $R^3$, $R^5$, $R^{10}$ and $R^{11}$ are as previously defined in Scheme (I). According to Scheme (III), uridine 31 has a C4 reactive center such that reaction with amine 22 yields N4-substituted cytidine 32. Acid-catalyzed deprotection of N4-substituted 32 yields N4-substituted cytosine 33, which may be subsequently halogenated at the C2-position and reacted with amine 24 to yield the cyclopentyl compound 25. Cyclopentyl compound 25 can be converted to desired 1-(2,4-pyrimidinediamino)-2-cyclopentane carboxamide 26 via conventional methods known to the skilled artisan.

Although Scheme (III) is exemplified with ribosylnucleosides, skilled artisans will appreciate that the corresponding 2'-deoxyribo and 2',3'-dideoxyribo nucleosides, as well as nucleosides including sugars or sugar analogs other than ribose, would also work.

Numerous uridines useful as starting materials in Schemes (III) are known in the art, and include, by way of example and not limitation, 5-bromouridine (Chem. Sources Int'l 2000; CAS Registry 957-75-5); 5-iodo-2'-deoxyuridine (Aldrich #1-775-6; CAS Registry 54-42-2); 5-fluorouridine (Aldrich #32,937-1; CAS Registry 316-46-1); 5-iodouridine (Aldrich #85,259-7; CAS Registry 1024-99-3); 5-(trifluoromethyl) uridine (Chem. Sources Int'l 2000; CAS Registry 70-00-8); 5-trifluoromethyl-2'-deoxyuridine (Chem. Sources Int'l 2000; CAS Registry 70-00-8). Additional uridines that can be used as starting materials in Scheme (III) and (VII) are available from General Intermediates of Canada, Inc., Edmonton, Calif. (www.generalintermediates.com) and/or Interchim, Cedex, France (www.interchim.com), or may be prepared using standard techniques. Myriad textbook references teaching suitable synthetic methods are provided infra.

Although many of the synthetic schemes discussed above do not illustrate the use of protecting groups, skilled artisans will recognize that in some instances certain substituents, such as, for example, $R^1$, may include functional groups requiring protection. The exact identity of the protecting group used will depend upon, among other things, the identity of the functional group being protected and the reaction conditions used in the particular synthetic scheme, and will be apparent to those of skill in the art. Guidance for selecting protecting groups and chemistries for their attachment and removal suitable for a particular application can be found, for example, in Greene & Wuts, supra.

Myriad references teaching methods useful for synthesizing pyrimidines generally, as well as starting materials described in Schemes (I)-(III), are known in the art. For specific guidance, the reader is referred to Brown, D. J., "The Pyrimidines", in *The Chemistry of Heterocyclic Compounds, Volume* 16 (Weissberger, A., Ed.), 1962, Interscience Publishers, (A Division of John Wiley & Sons), New York ("Brown I"); Brown, D. J., "The Pyrimidines", in *The Chemistry of Heterocyclic Compounds, Volume* 16, *Supplement I* (Weissberger, A. and Taylor, E. C., Ed.), 1970, Wiley-Interscience, (A Division of John Wiley & Sons), New York (Brown II"); Brown, D. J., "The Pyrimidines", in *The Chemistry of Heterocyclic Compounds, Volume* 16, *Supplement II* (Weissberger, A. and Taylor, E. C., Ed.), 1985, An Interscience Publication (John Wiley & Sons), New York ("Brown III"); Brown, D. J., "The Pyrimidines" in *The Chemistry of Heterocyclic Compounds, Volume* 52 (Weissberger, A. and Taylor, E.

C., Ed.), 1994, John Wiley & Sons, Inc., New York, pp. 1-1509 (Brown IV"); Kenner, G. W. and Todd, A., in *Heterocyclic Compounds*, Volume 6, (Elderfield, R. C., Ed.), 1957, John Wiley, New York, Chapter 7 (pyrimidines); Paquette, L. A., *Principles of Modern Heterocyclic Chemistry*, 1968, W. A. Benjamin, Inc., New York, pp. 1-401 (uracil synthesis pp. 313, 315; pyrimidine synthesis pp. 313-316; amino pyrimidine synthesis pp. 315); Joule, J. A., Mills, K. and Smith, G. F., *Heterocyclic Chemistry*, 3$^{rd}$ Edition, 1995, Chapman and Hall, London, UK, pp. 1-516; Vorbrüggen, H. and Ruh-Pohlenz, C., *Handbook of Nucleoside Synthesis*, John Wiley & Sons, New York, 2001, pp. 1-631 (protection of pyrimidines by acylation pp. 90-91; silylation of pyrimidines pp. 91-93); Joule, J. A., Mills, K. and Smith, G. F., *Heterocyclic Chemistry*, 4$^{th}$ Edition, 2000, Blackwell Science, Ltd, Oxford, UK, pp. 1-589; and *Comprehensive Organic Synthesis*, Volumes 1-9 (Trost, B. M. and Fleming, I., Ed.), 1991, Pergamon Press, Oxford, UK.

Additionally, the intermediates described throughout, as well as antiproliferative compounds derived therefrom, can be prepared by methods, including enzymatic methods, disclosed in U.S. Provisional application Ser. Nos. 10/628,401 and 10/628,199, filed Nov. 15, 2004, the contents of which are incorporated herein by reference.

5.4 Activity of the Antiproliferative Compounds

Active 1-(2,4-pyrimidinediamino)-2-cyclopentanecarboxamides typically inhibit proliferation of desired cells, such as tumor cells, with an IC$_{50}$ in the range of about 1 mM or less, as measured in a standard in vitro cellular proliferation assay. Of course, skilled artisans will appreciate that compounds which exhibit lower IC$_{50}$s, for example on the order of 100 μM, 10 μM, 1 μM, 100 nM, 10 nM, 1 nM, or even lower, may be particularly useful in therapeutic applications. The antiproliferative activity may be cytostatic or it may be cytotoxic. In instances where antiproliferative activity specific to a particular cell type is desired, the compound may be assayed for activity with the desired cell type and counter-screened for a lack of activity against other cell types. The desired degree of "inactivity" in such counter screens, or the desired ratio of activity vs. inactivity may vary for different situations, and may be selected by the user.

5.5 Uses of the Antiproliferative Compounds

The antiproliferative 1-(2,4-pyrimidinediamino)-2-cyclopentanecarboxamides prepared from intermediates described herein, including the various salts, prodrugs, hydrates and N-oxide forms thereof, may be used to inhibit cell proliferation in a variety of contexts. According to some embodiments of the method, a cell or population of cells is contacted with an amount of such a compound effective to inhibit proliferation of the cell or cell population. The compound may act cytotoxically to kill the cell, or cytostatically to inhibit proliferation without killing the cell.

6. EXAMPLES

The invention is further defined by reference to the following examples, which describe preparation of intermediates useful in the preparation of antiproliferative agents and methods for assaying for biological activity. It will be apparent to the skilled artisan that many modifications, both to the materials and methods may be practiced without departing from the scope of the invention.

Example 1

(1S, 2R)-1-(2,4-pyrimidinediamino)-2-cyclopentanecarboxamide (1)

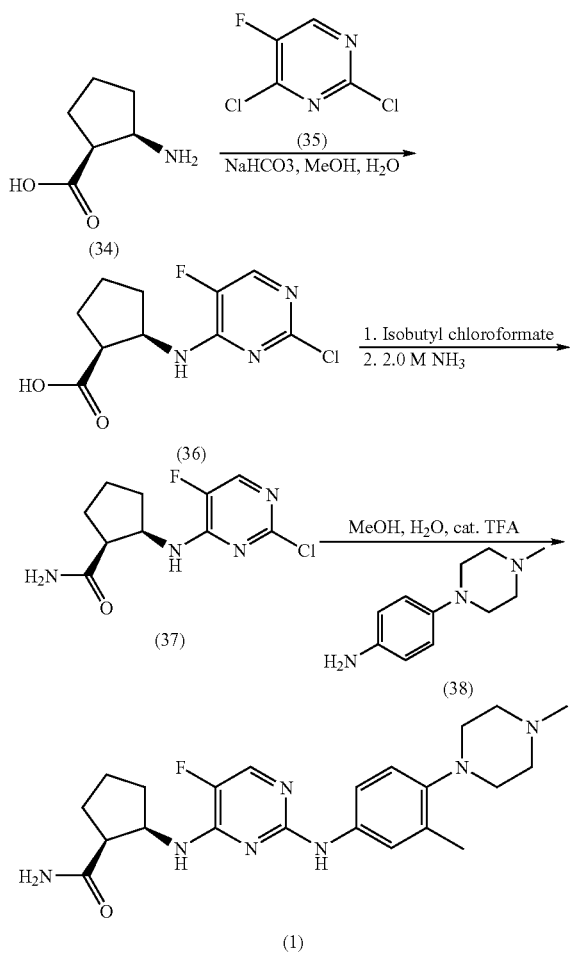

A mixture of (1S, 2R)-2-aminocyclopentanecarboxylic acid HCl salt (100 mg) (34), 2,4-dichloro-5-fluoropyrimidine (200 mg) (35), sodium bicarbonate (50 mg), methanol (5 mL) and water (1 mL) was stirred, with warming, from room temperature to 60° C. overnight. The reaction solution was evaporated to give (1S, 2R)-cyclopentanecarboxylic acid (36).

The crude residue (36) was dissolved in dichloromethane (10 mL) and isobutyl chloroformate (0.15 mL) and diisopropylethylamine (0.27 mL) were added. The reaction mixture was stirred at ambient temperature for 30 minutes, quenched with 2.0M ammonia in methanol (10 ml), stirred at room temperature for 30 minutes, diluted with water (100 mL) and extracted with ethyl acetate (2×100 mL). The combined organic layers were evaporated to provide crude (1S, 2R)-carboxamide (37).

(1S, 2R)-carboxamide (37) was reacted with 3-methyl-4-(4-methyl)piperazinoaniline (38) in a solution of methanol (5 mL) and water (0.5 mL) with catalytic amount of trifluoroacetic acid at 100° C. overnight. The reaction mixture was evaporated and purified by flash chromatography (2.0 MNH$_3$ in methanol in $CH_2Cl_2$=1-5%). Recrystallization from ethyl acetate and hexanes gave (1S,2R) carboxamide (1) (30 mg) as a white solid.

Example 2

(1R, 2S)-1-(2,4-pyrimidinediamino)-2-cyclopentanecarboxamide (2)

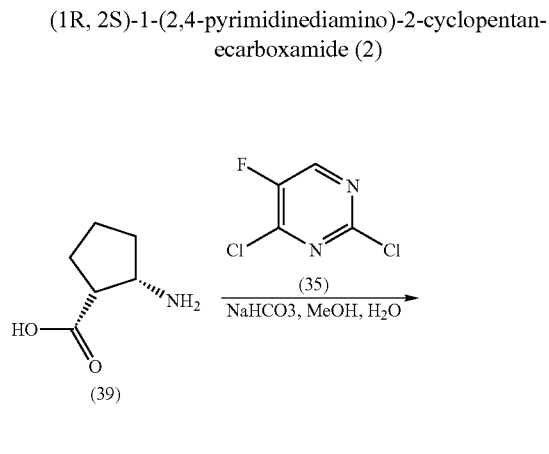

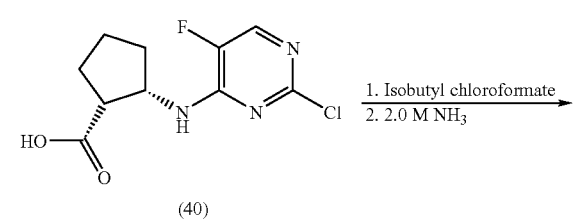

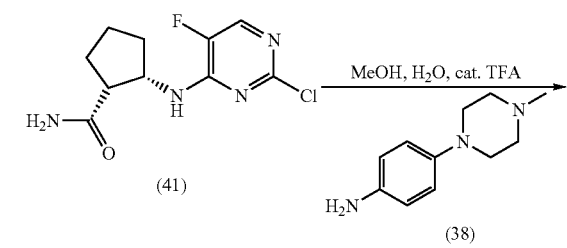

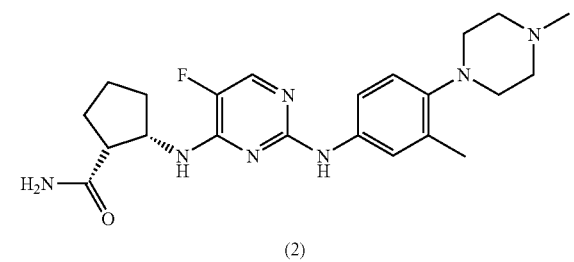

Using the method of Example 1, and starting with (1R, 2S)-2-aminocyclopentane carboxylic acid (39) (250 mg) gave the title compound (2) as a white solid (10 mg).

Example 3

(1S, 2S)-1-(2,4-pyrimidinediamino)-2-cyclopentanecarboxamide (3)

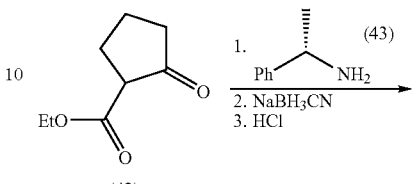

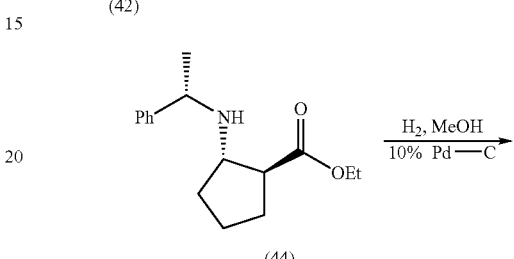

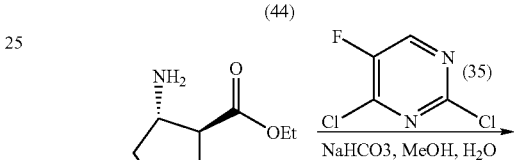

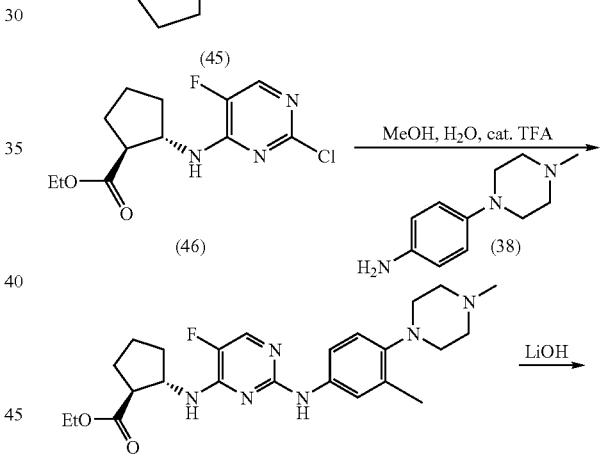

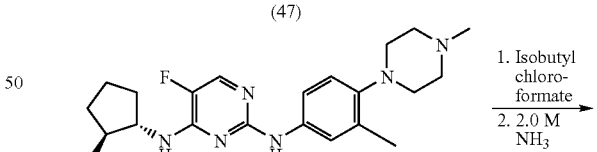

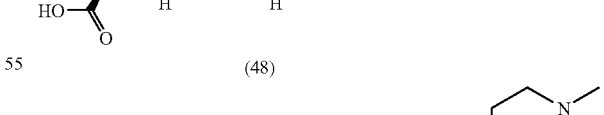

Ethyl (1S, 2S)-2-aminocyclopentanecarboxylate was made according to the procedure of Gellman et al., *J. Org. Chem.* 2001, 66, 5629-5632. The ethyl ester of 2-carboxy cyclopentanone (42) (4 mL), (S)-(-)-methylbenzylamine (6.96 mL) (43) and glacial acetic acid (3.08 mL) were dissolved in ethanol (32 mL) and stirred at room temperature overnight. The reaction solution was diluted with ethanol (64 ml) and heated to 72° C. Then NaBH$_3$CN (4.24 g) was added in portions and mixture was stirred at 72° C. for 5 h. Water (150 mL) was added and ethanol was removed in vacuo. The remaining aqueous solution was extracted with ether (2×150 mL) and the ether layer was passed through a silica plug, which was eluted with ether (150 mL). The filtrate was evaporated and the residual oil was dissolved in ethyl acetate (120 mL). Then 4.0 N HCl in dioxane (6.5 mL) was added dropwise with stirring. The solution was kept at 0° C. for 1 h, the white precipitate was then filtered and washed with ethyl acetate. The resulting white solid was recrystallized from ethanol (6.5 g in 40 mL ethanol). The product was further recrystallized from acetonitrile to give the HCl salt of the ethyl ester of benzylated β-aminocyclopentanecarboxylate (44).

The HCl salt of the ethyl ester of benzylated β-amino cyclopentane carboxylate (44) (300 mg) was dissolved in methanol and 10% Pd—C was added. The solution was shaken under H$_2$ at 50 psi for 3 days, filtered through Celite and washed with methanol. The filtrate was evaporated to give the ethyl ester of β-amino cyclopentane carboxylate (45).

A mixture of the HCl salt of ethyl ester of β-amino cyclopentane carboxylate (45), 2,4-dichloro-5-fluoropyrimidine (35) (200 mg), sodium bicarbonate (100 mg), methanol (5 mL) and water (1 mL) were stirred at room temperature overnight. The reaction solution was diluted with water (100 mL). The aqueous solution was extracted with ethyl acetate (2×100 mL) and the organic layers were evaporated to give the mono-SNAr product (46).

The mono-SNAr product (46) was reacted with 3-methyl-4-(4-methyl)piperazinoaniline (38) in a solution of methanol (1 mL) and water (0.2 mL) with catalytic amount of trifluoroacetic acid at 100° C. overnight. The reaction mixture was evaporated and purified by flash column chromatography (2.0 MNH$_3$ in methanol in CH$_2$Cl$_2$=1-3%) to give (1S, 2S)-ethylcyclopentanecarboxylate (47).

(1S, 2S)-ethylcyclopentanecarboxylate (47) (100 mg) was dissolved in a solution of THF/MeOH/H$_2$O 6:3:1 and LiOH (46 mg) was added. The reaction solution was stirred at room temperature overnight, neutralized with 1N HCl and the pH of the aqueous solution was adjusted to pH 6. The solvent was evaporated and the solid recrystallized from methanol and ethyl acetate to give (1S, 2S)-cyclopentanecarboxylic acid (48).

(1S, 2S)-cyclopentanecarboxylic acid (48) (100 mg) in dichloromethane (10 mL) was treated with diisopropylethylamine (0.08 mL) and isobutyl chloroformate (0.045 mL) and the reaction mixture stirred at room temperature for 30 minutes, quenched with 2.0 M NH$_3$ in methanol (10 mL), stirred at room temperature for 30 minutes and then evaporated. The residue was purified by flash chromatography (2.0 M NH$_3$ in methanol in CH$_2$Cl$_2$=1-5%). Recrystallization from ethyl acetate and hexanes gave (1S, 2S)-1-(2,4-pyrimidinediamino)-2-cyclopentanecarboxamide (3) as a white solid.

Example 4

(1R, 2R)-1-(2,4-pyrimidinediamino)-2-cyclopentanecarboxamide (4)

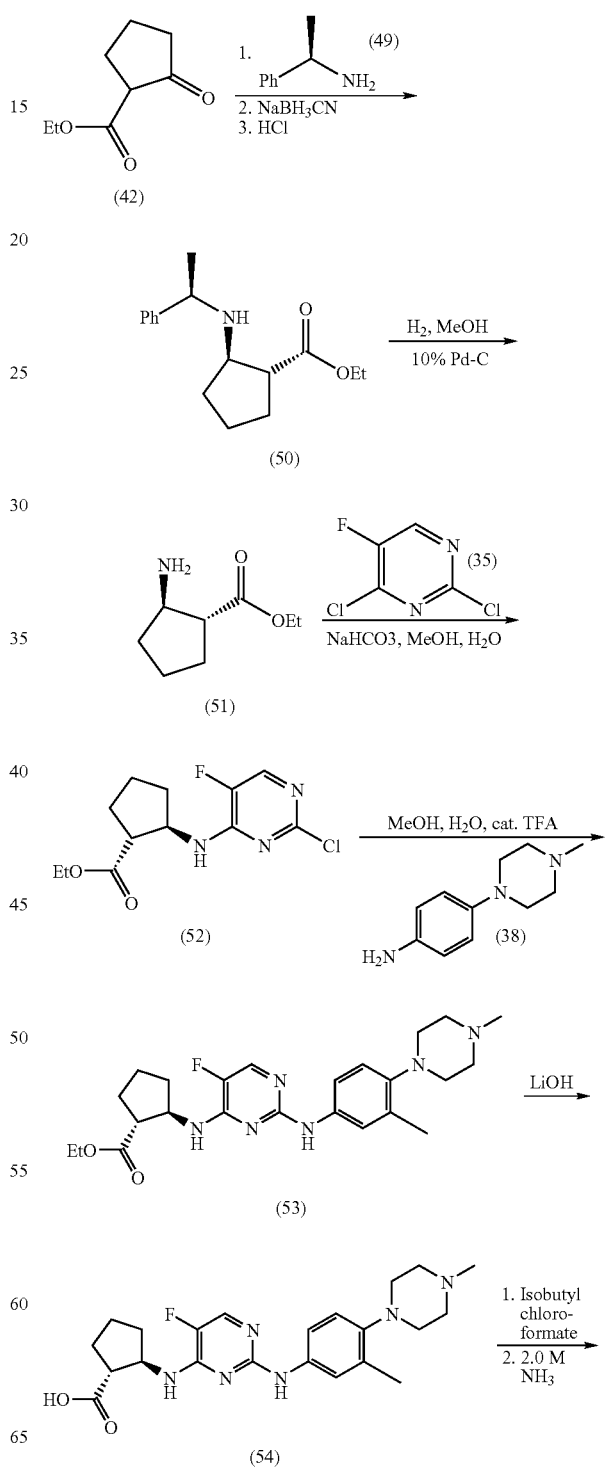

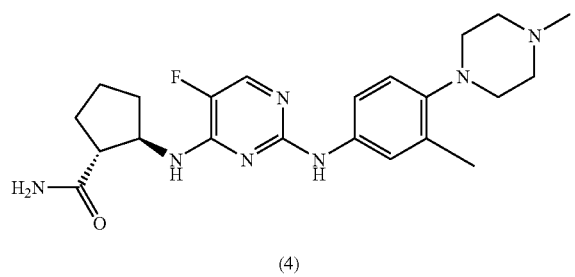

(4)

Using (R)-(+)-methylbenzylamine (6.96 mL) instead of (S)-(+)-methylbenzylamine in the first step and following the procedure of Example 3 gave (1R, 2R)-1-(2,4-pyrimidinediamino)-2-cyclopentanecarboxamide (4) (30 mg).

Example 5

Synthesis of (1S, 2R)-1-(2,4-pyrimidinediamino)-2-cyclopentanecarboxamide (1)

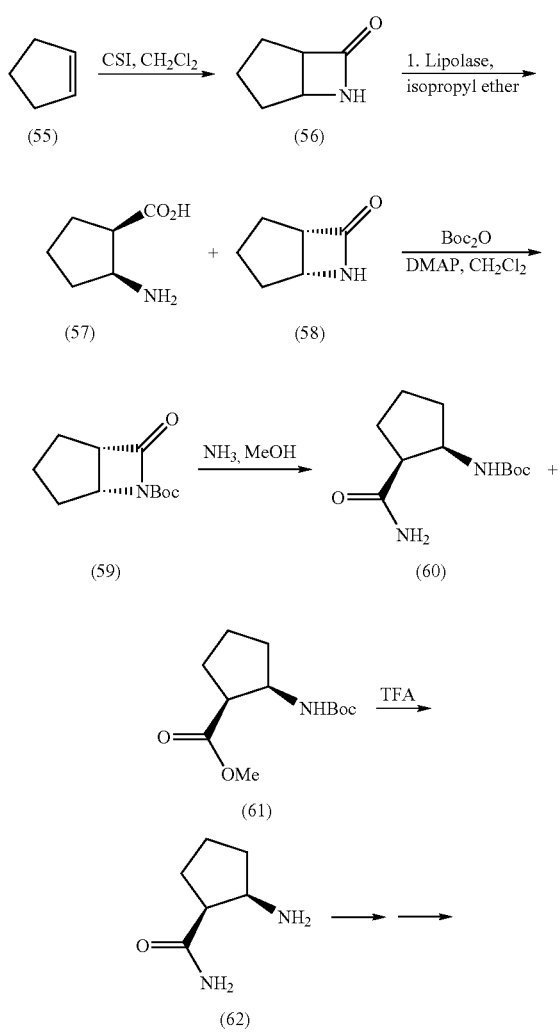

(1)

Cyclopentene (55) (18.7 mL) and chloro sulfonyl isocyanate (18.4 mL) were dissolved in dichloromethane (30 mL) at 0° C. and stirred for 1 h. The reaction mixture was heated to 40° C. for 24 h, quenched slowly with cold water in an ice bath and then added dropwise to a solution of $Na_2SO_3$ (13.36 g) in water (40 ML) at 0° C. Meanwhile, 20% NaOH aqueous solution (125 mL) was added to keep the pH of the solution at 5-7. The temperature was the solution was controlled to remain below 25° C. After addition, the solution was stirred for 1 h at 0° C. and extracted with dichloromethane (2×200 mL). The dichloromethane solution was evaporated and recrystallized from ether and hexanes to give the β-lactam of cyclopentane (56) as a solid (10 g).

Racemic (56) (4 g) was dissolved in isopropyl ether (80 mL). Lipolase (lipase on acrylic resin, 4 g) and water (0.32 mL) was added. The reaction solution was stirred at 60° C. for 10 days. The solid was filtered off and washed with isopropyl ether. The filtrate was evaporated and recrystallized from isopropyl ether and hexanes to give a light yellow solid as product (58) (2 g).

Compound (58) (2 g) was dissolved in dichloromethane (20 mL) followed by addition of $Boc_2O$ (4.4 g) and dimethylaminopyridine (0.22 g). The reaction mixture was stirred at room temperature overnight, diluted with ethyl acetate (100 mL), washed with water (100 mL) and brine (100 mL). Ethyl acetate was evaporated and the resulting mixture was passed through a short silica gel column, eluting with 1:1 ethyl acetate and hexanes. The solvent was removed in vacuo and recrystallized from hexanes to give white solid (59) as product.

Compound (59) was dissolved in 2.0M NH3 in methanol (30 mL) and reacted at room temperature overnight. The solution was evaporated and recrystallized from ethyl acetate/hexanes to give white solid (60) (800 mg). The filtrate was evaporated to give the corresponding methyl ester of (60) as an oil.

Compound (60) (800 mg) was reacted in 4.0 M HCl in dioxane (10 mL) at room temperature for 2 h and the solution was evaporated to give the HCl salt of (62).

The HCl salt of (62) was dissolved in methanol (10 mL) and water (1 mL). 2,4-dichloro-5-fluoropyrimidine (1 g) and sodium bicarbonate (500 mg) were added to the solution and stirred at room temperature overnight. The solution was diluted with water (100 mL) and extracted with ethyl acetate (3×100 mL). The organic layers were evaporated and recrystallized from ethyl acetate/hexanes to give a white solid as mono-SNAR product (750 mg).

4-Fluoro-3-methylnitrobenzene (4 g) was dissolved in methanol (10 mL) and methylpiperazine (4 mL) was added to the solution, which was heated at 100° C. overnight and then diluted with water (100 mL). The solution was extracted with ethyl acetate (2×100 mL), the organic extracts were evaporated and recrystallized from ethyl acetate/hexanes to give as yellow solid 3-methyl-4-(4-methyl)piperazinonitrobenzene. The solid was dissolved in methanol (50 mL) and 10% Pd—C was added. The reaction solution was reacted under 40 psi $H_2$ for 1 h. The catalyst was removed by filtration and washed with methanol. The filtrate was evaporated to give 3-methyl-4-(4-methyl)piperazinoaniline.

The mono-SNAr product (700 mg) was reacted with 3-methyl-4-(4-methyl)piperazinoaniline in a solution of methanol (5 mL) and water (0.5 mL) with catalytic amount of trifluoroacetic acid at 100° C. overnight. The reaction mixture was evaporated and purified by flash column chromatography (2.0 $MNH_3$ in methanol in $CH_2Cl_2$=1-7%). Recrystallization from ethyl acetate and hexanes gave a white solid (1) (700 mg).

Compound (1) was dissolved in methanol (10 mL) and reacted with 4.0M HCl in dioxane (0.9 mL) at room temperature for 30 min. The solution was evaporated and dried to solid. Recrystallization from cold methanol and ethyl acetate gave the HCl salt of (1).

Example 6

Anti-Proliferation Assays for the Stereoisomers of (1S, 2R)-1-(2,4-pyrimidinediamino)-2-cyclopentanecarboxamide (1), (2), (3) and (4)

The four stereoisomers isomers of (1S, 2R)-1-(2,4-pyrimidinediamino)-2-cyclopentanecarboxamide (1), (2), (3) and (4) were prepared as described in Examples 1-4. The racemic mixture of the cis compound was prepared as described herein. The $IC_{50}$ values of various compounds against different tumor cell lines were determined using standard in vitro antiproliferation assays. The tumor cell lines tested were as follows: A549 (lung); H1299 (lung); DU145 (prostate); HCT116 (colon/p53wt); and mirapaca.

TABLE 1

| Stereoisomer | A549 | H1299 | Du145 | HCT116 | Mirapaca |
|---|---|---|---|---|---|
| 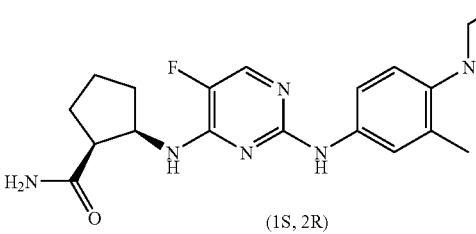 (1S, 2R) (1) | <1 μM | <1 μM | <1 μM | <0.1 μM | |
| 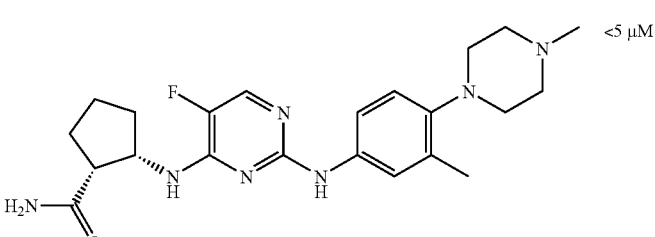 (1S, 2R) (2) | <5 μM | <10 μM | | | |
| Racemic cis (1) and (2) | <1 μM | <1 μM | <1 μM | <0.1 μM | |
| 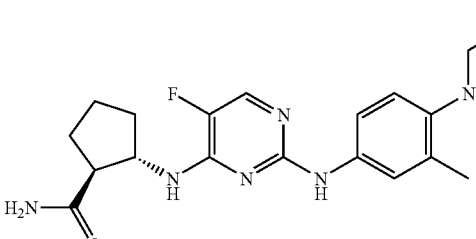 (1S, 2R) (4) | >20 μM | >20 μM | | | |

TABLE 1-continued

| Stereoisomer | A549 | H1299 | Du145 | HCT116 | Mirapaca |
|---|---|---|---|---|---|
| 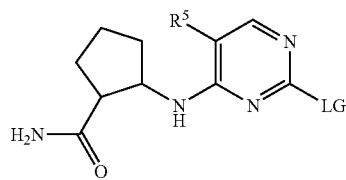 (1S, 2R) (3) | <5 µM | <5 µM | <5 µM | <5 µM | |

As can be seen from TABLE 1, the trans (1S, 2S) is inactive in the measured assays while the other three stereoisomers have significant activity in the antiproliferative screens.

Although the foregoing inventions have been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

All literature and patent references cited throughout the application are incorporated by reference into the application for all purposes.

Column 36, lines 6-15, please delete the chemical structure labeled as formula (II) and replace it with the following:
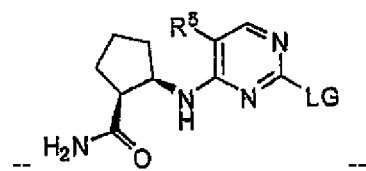

What is claimed is:

1. A compound according to structural formula (I):

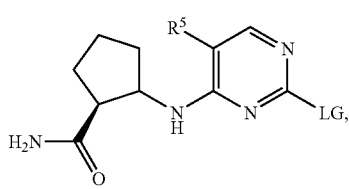

(I)

or a pharmaceutically acceptable salt or N-oxides thereof, wherein:

$R^5$ is halo, —CN, —NO$_2$, CO$_2$R$^a$ or —CF$_3$;

$R^a$ is selected from the group consisting of hydrogen, lower alkyl and lower cycloalkyl; and LG is —S(O)$_2$Me, —SMe, or a halide, wherein the compound is enriched in one or more of the following stereoisomers according to structural formulae (II), (III) or (IV):

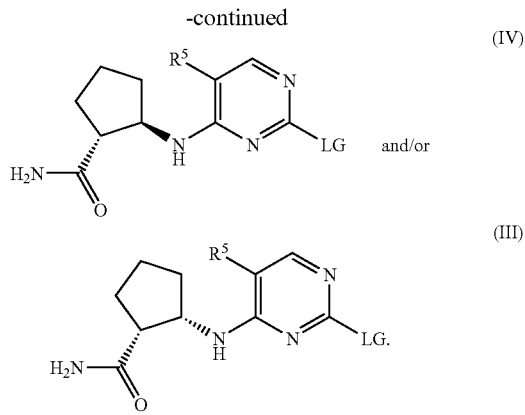

2. The compound of claim 1 in which $R^5$ is fluoro.

3. The compound of claim 1 in which $R^5$ is fluoro and LG is a halide.

4. A compound according to structural formula (II):

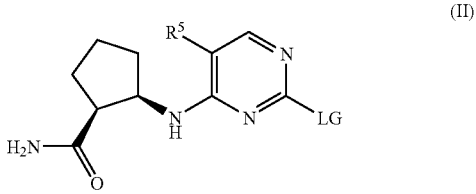

(II)

or a pharmaceutically acceptable salt or N-oxides therof, which is substantially free of the enantiomer and any diastereomers thereof, wherein $R^5$ and LG are as defined in claim 1.

5. A compound according to structural formula (III):

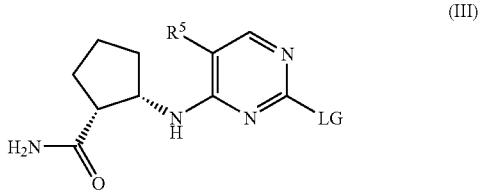

(III)

6. A compound according to structural formula (IV):

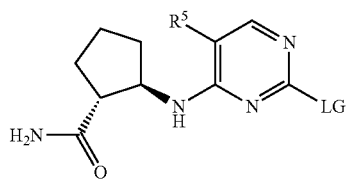

or a pharmaceutically acceptable salt or N-oxides thereof, which is substantially free of the enantiomer and any diastereomers thereof wherein $R^5$ and LG are as defined in claim 1.

7. The compound of any one of claims 4-6 in which $R^5$ is fluoro.

8. The compound of any one of claims 4-6 in which $R^5$ is fluoro and LG is a halide.

9. The compound of claim 1 in which a compound according to structural formula (I) is substantially free of a compound according to structural formula (V):

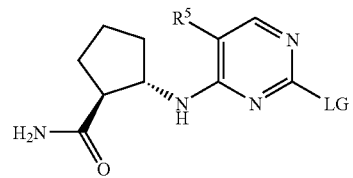

or a pharmaceutically acceptable salt or N-oxides thereof.

10. A compound according to structural formula (I) as defined in claim 9 which is enriched in one or more of the following stereoisomers according to structural formulae (II), (III) or (IV):

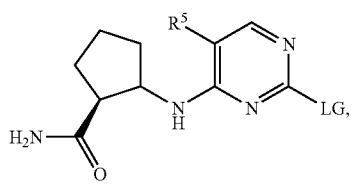

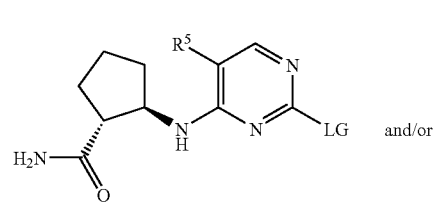

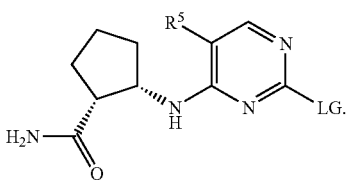

11. The compound of claim 9 or 10 in which $R^5$ is fluoro.

12. The compound of claims 9 or 10 in which $R^5$ is fluoro and LG is a halide.

* * * * *

UNITED STATES PATENT AND TRADEMARK OFFICE
CERTIFICATE OF CORRECTION

| | |
|---|---|
| PATENT NO. | : 7,511,137 B2 |
| APPLICATION NO. | : 11/016403 |
| DATED | : March 31, 2009 |
| INVENTOR(S) | : Hui Li |

It is certified that error appears in the above-identified patent and that said Letters Patent is hereby corrected as shown below:

Column 2, lines 58-67, please delete the chemical structure labeled as formula (II) and replace it with the following:

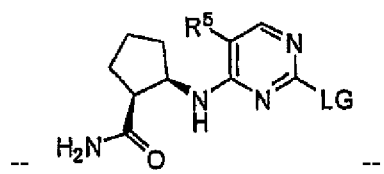

Column 11, lines 25-35, please delete the chemical structure labeled as formula (II) and replace it with the following:

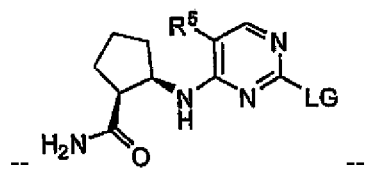

Column 33, lines 58-67, please delete the chemical structure labeled as formula (II) and replace it with the following:

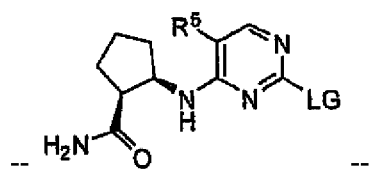

Signed and Sealed this
Fifteenth Day of May, 2012

David J. Kappos
*Director of the United States Patent and Trademark Office*